(12) United States Patent
Poulin et al.

(10) Patent No.: US 11,134,728 B1
(45) Date of Patent: Oct. 5, 2021

(54) CUSTOMIZABLE RESPIRATORY PROTECTION DEVICE

(71) Applicants: Shawn Gregory Poulin, Arlington, VA (US); Andre Gregory Joseph, Bowie, MD (US)

(72) Inventors: Shawn Gregory Poulin, Arlington, VA (US); Andre Gregory Joseph, Bowie, MD (US)

(*) Notice: Subject to any disclaimer, the term of this patent is extended or adjusted under 35 U.S.C. 154(b) by 0 days.

(21) Appl. No.: 16/945,623

(22) Filed: Jul. 31, 2020

(51) Int. Cl.
| | | |
|---|---|---|
| *A41D 13/11* | (2006.01) | |
| *A41D 11/00* | (2006.01) | |
| *A62B 18/08* | (2006.01) | |
| *A61N 2/00* | (2006.01) | |
| *A62B 23/02* | (2006.01) | |
| *A62B 18/02* | (2006.01) | |
| *A61N 2/06* | (2006.01) | |

(52) U.S. Cl.
CPC .......... *A41D 13/1107* (2013.01); *A41D 11/00* (2013.01); *A41D 13/1161* (2013.01); *A61N 2/004* (2013.01); *A61N 2/06* (2013.01); *A62B 18/025* (2013.01); *A62B 18/08* (2013.01); *A62B 23/02* (2013.01)

(58) Field of Classification Search
CPC ............ A61M 16/047; A61M 16/0627; A61M 16/06; A41D 13/1107; A41D 13/1161; A41D 11/00; A41D 1/00; A41D 13/11–1192; A61F 9/02; A61F 9/04; A62B 18/00; A62B 18/025; A62B 18/08; A62B 23/02; A62B 18/02; A62B 18/082; A62B 23/025; A61N 2/06; A41G 7/00; A41G 7/02

USPC ........ 128/857, 858, 206.21, 206.23, 206.24, 128/206.28; 2/410, 6.3, 6.5, 8.2, 424, 2/427, 428, 429, 431, 9; 602/17, 74
See application file for complete search history.

(56) References Cited

U.S. PATENT DOCUMENTS

| | | | | |
|---|---|---|---|---|
| 5,694,925 | A * | 12/1997 | Reese ................. | A41D 13/1115 128/206.19 |
| 6,532,598 | B1 * | 3/2003 | Cardarelli .............. | A41D 13/11 128/206.19 |
| 2007/0101996 | A1 * | 5/2007 | Carstens ............ | A41D 13/1161 128/206.12 |
| 2010/0224199 | A1 * | 9/2010 | Smith ................. | A61M 16/142 128/863 |
| 2014/0259253 | A1 * | 9/2014 | Jacob ................. | A41D 13/1184 2/15 |
| 2018/0146733 | A1 * | 5/2018 | Greenblat .......... | A41D 13/1153 |
| 2018/0296864 | A1 * | 10/2018 | Feasey ................. | A62B 18/025 |
| 2019/0009114 | A1 * | 1/2019 | Han ...................... | A41D 1/002 |
| 2020/0030562 | A1 * | 1/2020 | Waterford .......... | A61M 16/0616 |

* cited by examiner

*Primary Examiner* — Caitlin A Carreiro
(74) *Attorney, Agent, or Firm* — The Iwashko Law Firm, PLLC; Lev Ivan Gabriel Iwashko

(57) ABSTRACT

A customizable respiratory protection device, including a mouth portion, including a mouth body to cover a mouth and a nose of a user, a filter receiving portion disposed on at least a portion of a rear surface of the mouth body to store an air filter therein, and an aperture disposed on an end of the filter receiving portion to receive the air filter therethrough, an attachment portion to cover eyes and a forehead of the user; and at least one fastener removably disposed on at least a portion of the mouth body to receive the attachment portion thereon, such that the attachment portion connects to the mouth body.

5 Claims, 2 Drawing Sheets

CUSTOMIZABLE RESPIRATORY PROTECTION DEVICE

BACKGROUND

1. Field

The present general inventive concept relates generally to a protection device, and particularly, to a customizable respiratory protection device.

2. Description of the Related Art

A pathogen that has been identified as severe acute respiratory syndrome coronavirus 2 (SARS-CoV-2) causes a disease known as coronavirus disease 2019 (COVID-19). The disease is highly infectious and transmission between humans often occurs during close human contact. More specifically, an infected person communicating to an uninfected person within six feet is likely to infect the uninfected person.

Additional factors also play a role, such as an outdoor location versus an indoor location, state of an immune system, and/or use of personal protective equipment.

The COVID-19 pandemic has impacted the lives of many people worldwide. However, protecting people from spreading SARS-CoV-2 is important to prevent certain people who may be at a substantial risk from developing severe complications. One method of preventing the spread of SARS-CoV-2 is through the use of a face mask. A face mask is a type of personal protective equipment (PPE) that is worn by a user to reduce and/or prevent ejection of particles from a mouth of the user, such that the face mask obstructs movement of the particles.

Children are a tricky demographic to manage regarding the face mask. Many children refuse to wear the face mask because it is uncomfortable and otherwise lacks appeal to the child. Also, in some cases, the face mask makes it difficult for children to communicate.

Therefore, there is a need for a respiratory protection device that can be customized and provide protection that appeals to children, as well as, being comfortable to wear.

SUMMARY

The present general inventive concept provides a customizable respiratory protection device.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a customizable respiratory protection device, including a mouth portion, including a mouth body to cover a mouth and a nose of a user, a filter receiving portion disposed on at least a portion of a rear surface of the mouth body to store an air filter therein, and an aperture disposed on an end of the filter receiving portion to receive the air filter therethrough, an attachment portion to cover eyes and a forehead of the user; and at least one fastener removably disposed on at least a portion of the mouth body to receive the attachment portion thereon, such that the attachment portion connects to the mouth body.

The filter receiving portion may dissipate moisture to an outer surface of the mouth body.

The at least one fastener may be a magnet.

The at least one fastener may increase blood flow within a face of the user using magnet therapy.

The customizable respiratory protection device may further include a plurality of head fasteners disposed on at least a portion of each edge of the mouth body to wrap around a head of the user.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

List of Components
Customizable Respiratory Protection Device 100
Mouth Portion 110
Mouth Body 111
Filter Receiving Portion 112
Aperture 113
Attachment Portion 120
Attachment Body 121
Eye Holes 122
Fasteners 130
Head Fasteners 140

Figure 1:
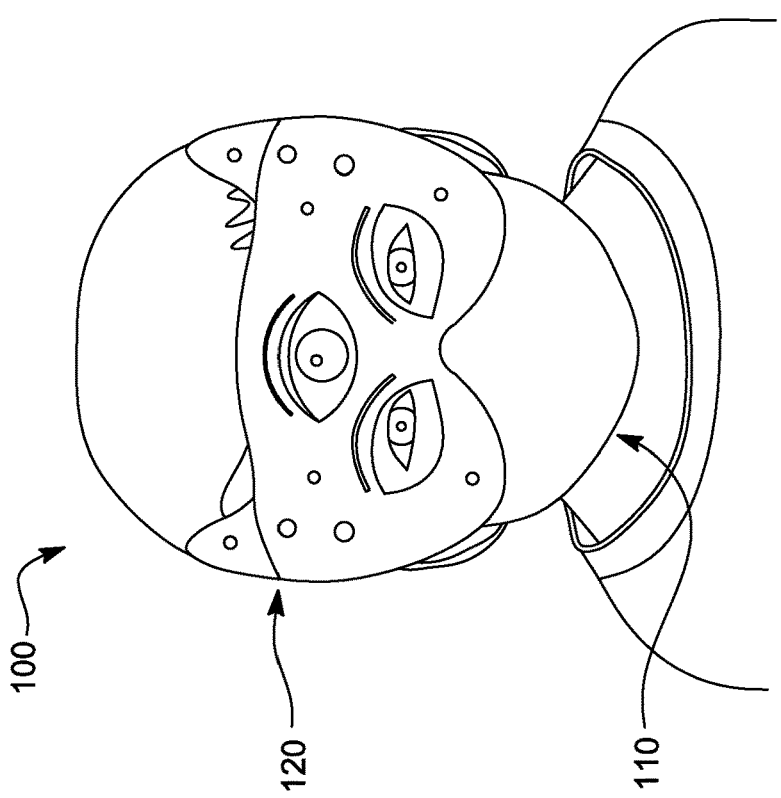
FIG. 1 illustrates a front elevation view of a customizable respiratory protection device, according to an exemplary embodiment of the present general inventive concept.

FIG. 1 illustrates a front elevation view of a customizable respiratory protection device 100, according to an exemplary embodiment of the present general inventive concept.

The customizable respiratory protection device 100 may be constructed from at least one of metal, plastic, cloth, and rubber, etc., but is not limited thereto.

The customizable respiratory protection device 100 may include a mouth portion 110, an attachment portion 120, a plurality of fasteners 130, and a plurality of head fasteners 140, but is not limited thereto.

The mouth portion 110 and/or the attachment portion 120 may have a range of predetermined sizes to fit a head of a user, such as a child. In other words, the mouth portion 110 and/or the attachment portion 120 may be too small to fit an adult.

Figure 2A:
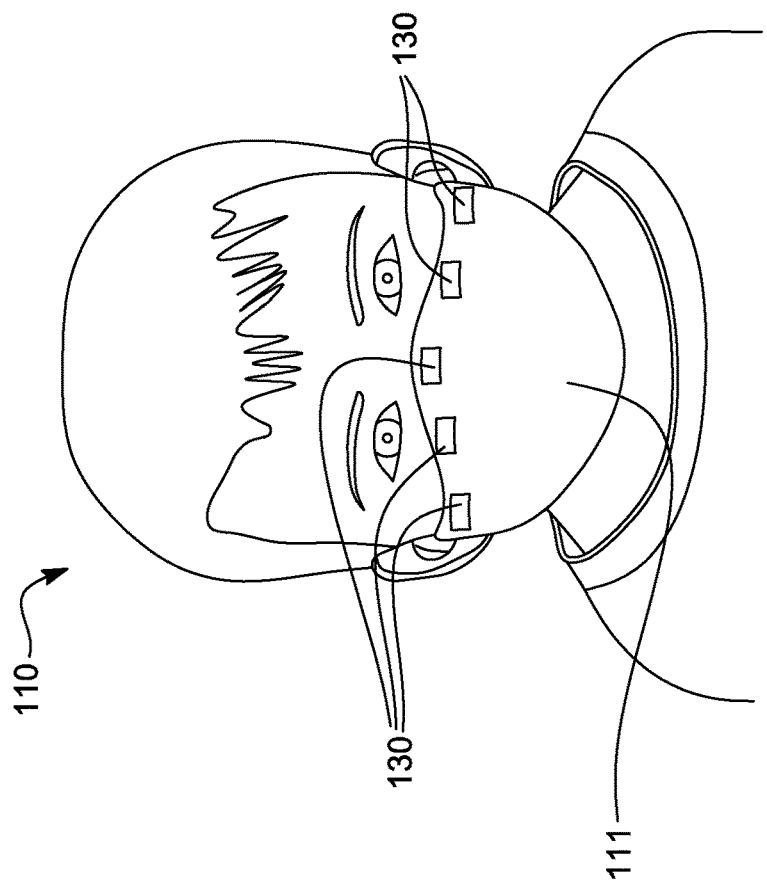
FIG. 2A illustrates a front elevation view of a mouth portion, according to an exemplary embodiment of the present general inventive concept.

FIG. 2A illustrates a front elevation view of a mouth portion 110, according to an exemplary embodiment of the present general inventive concept.

Figure 2B:
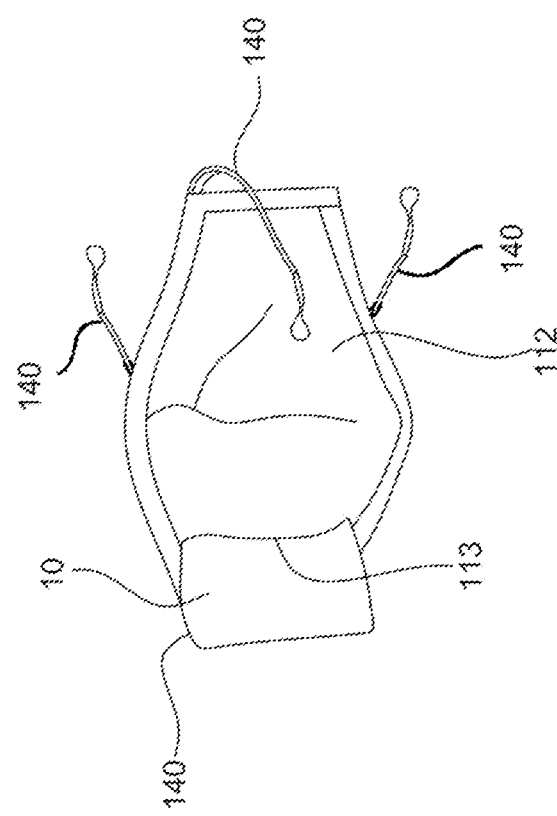
FIG. 2B illustrates a rear elevation view of the mouth portion, according to an exemplary embodiment of the present general inventive concept.

FIG. 2B illustrates a rear elevation view of the mouth portion 110, according to an exemplary embodiment of the present general inventive concept.

The mouth portion 110 may include a mouth body 111, a filter receiving portion 112, and an aperture 113, but is not limited thereto.

The mouth body 111 may cover at least a portion of a mouth and/or a nose of the user. Moreover, the mouth body 111 may be constructed to facilitate breathing therefrom. However, the mouth body 111 may reduce and/or prevent at least one particle (e.g., bacteria, fungi, parasites, viruses, etc.) from moving therethrough. Furthermore, the mouth body 111 may allow air to be inhaled therethrough.

The mouth body 111 may have any design thereon based on a preference of the user. For example, the mouth body 111 may appear as having a theme, a persona (e.g., superhero), and/or an animal. As such, the mouth body 111 may encourage use by children due to appearing as a design favored by the user.

The filter receiving portion 112 may be disposed on at least a portion of a rear surface of the mouth body 111. The filter receiving portion 112 may be constructed of polyester, spandex, Lycra™, and/or elastane to absorb moisture and dissipate moisture toward an outer surface of the mouth body 111. As such, the filter receiving portion 112 may prevent accumulation of moisture on a rear surface thereof, such as moisture from breath of the user.

The aperture 113 may be disposed on at least a portion of an end of the filter receiving portion 112. The aperture 113 may receive an air filter 10 therethrough, such that the filter receiving portion 112 may store the air filter 10 therein. For example, the filter receiving portion 112 may store an N95 mask, N95 filter, and/or any other type of filter to prevent the at least one particle from moving therethrough.

Figure 3:
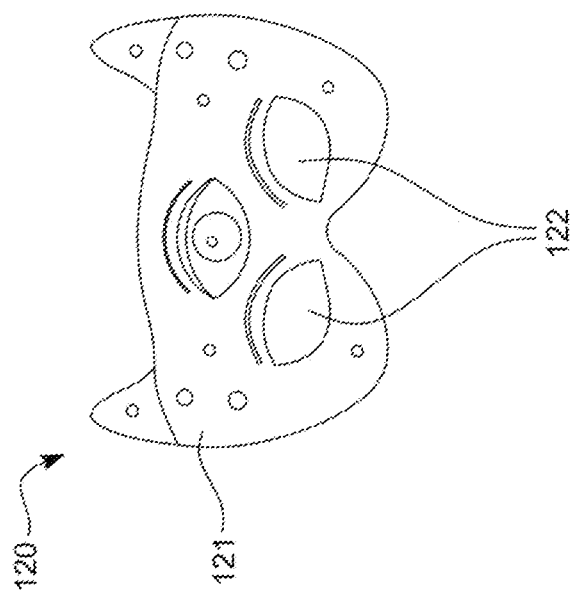
FIG. 3 illustrates a front elevation view of an attachment portion, according to an exemplary embodiment of the present general inventive concept.

FIG. 3 illustrates a front elevation view of an attachment portion 120, according to an exemplary embodiment of the present general inventive concept.

The attachment portion 120 may include an attachment body 121 and a plurality of eye holes 122, but is not limited thereto.

The attachment body 121 may cover at least a portion of the head of the user, such as eyes and/or a forehead of the user. Moreover, the attachment body 121 may be removably disposed on at least a portion of the mouth body 111. The attachment body 121 may have any design thereon based on the preference of the user. For example, the attachment body 121 may appear as a theme, a persona (e.g., superhero), and/or an animal. As such, the attachment body 121 may encourage use by children due to appearing as a design favored by the user.

The plurality of eye holes 122 may be disposed on at least a portion of the attachment body 121. Also, the plurality of eye holes 122 may allow the eyes of the user to see therethrough.

Each of the plurality of fasteners 130 may include a button, an adhesive, hooks and loops, and a magnet, but is not limited thereto.

The plurality of fasteners 130 may be removably disposed on at least a portion of the mouth body 111. Additionally, the plurality of fasteners 130 may receive at least a portion of a rear surface of the attachment body 121 thereon, such that the plurality of fasteners 130 connect the attachment body 121 to the mouth body 111.

Furthermore, the plurality of fasteners 130 may correspond to another plurality of fasteners disposed on the attachment body 121. For example, each magnet of the plurality of fasteners 130 may connect to each magnet of the another plurality of fasteners on the attachment body 121.

Also, each magnet of the plurality of fasteners 130 may improve health of the user through magnet therapy. More specifically, each magnet of the plurality of fasteners 130 may increase blood flow within a face of the user. As such, the plurality of fasteners 130 may soothe and/or relax the face of the user.

The plurality of head fasteners 140 may include a rope, a twine, a rubber band, a magnet, and an adhesive, but is not limited thereto.

The plurality of head fasteners 140 may be disposed on at least a portion of each edge of the mouth body 111. The plurality of head fasteners 140 may wrap around at least a portion of a head of the user. In particular, the plurality of head fasteners 140 may cover a perimeter of the head of the user, instead of ears of the user. As such, the plurality of head fasteners 140 may prevent discomfort on the ears of the user.

Therefore, the customizable respiratory protection device 100 may be customized using different types of the mouth portion 110 and/or the attachment portion 120. Also, the customizable respiratory protection device 100 may prevent inhalation and/or exhalation of the at least one particle.

The present general inventive concept may include a customizable respiratory protection device 100, including a mouth portion 110, including a mouth body 111 to cover a mouth and a nose of a user, a filter receiving portion 112 disposed on at least a portion of a rear surface of the mouth body 111 to store an air filter 10 therein, and an aperture 113 disposed on an end of the filter receiving portion 112 to receive the air filter 10 therethrough, an attachment portion 120 to cover eyes and a forehead of the user; and at least one fastener 130 removably disposed on at least a portion of the mouth body 111 to receive the attachment portion 120 thereon, such that the attachment portion 120 connects to the mouth body 111.

The filter receiving portion 112 may dissipate moisture to an outer surface of the mouth body 111.

The at least one fastener 130 may be a magnet.

The at least one fastener 130 may increase blood flow within a face of the user using magnet therapy.

The customizable respiratory protection device 100 may further include a plurality of head fasteners 140 disposed on at least a portion of each edge of the mouth body 111 to wrap around a head of the user.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A customizable respiratory protection device, comprising:
   a mouth portion, comprising:
   a mouth body configured to cover a mouth and a nose of a user and constructed to facilitate breathing through an entire surface area of the mouth body such that the mouth body prevents at least one particle of at least one of a bacteria, a virus, a parasite, and a fungus from moving through the entire surface area of the mouth body and allows air to be inhaled through the entire surface area of the mouth body,
   a filter receiving portion constructed of spandex and disposed on at least a portion of a rear surface of the mouth body, wherein an aperture is disposed on an end of the filter receiving portion to receive an air filter therethrough such that the filter receiving portion stores the air filter therein;
   an attachment portion comprising:
   an attachment body comprising an upper edge configured for placement at the top of the forehead of the user and a lower edge configured to extend across the bridge of the nose and the cheeks of the user below the eyes such that the attachment body is configured to extend from above the nose of the user, around each eye, and across the entire forehead of the user to cover the face and forehead of the user, and
   a plurality of eye holes disposed on at least a portion of the attachment body to allow the eyes of the user to see therethrough; and
   a plurality of fasteners removably disposed on at least a portion of the mouth body and configured to receive at least a portion of a rear surface of the attachment body thereon such that the plurality of fasteners connect the attachment body to the mouth body.

2. The customizable respiratory protection device of claim 1, wherein the at least one fastener is a magnet.

3. The customizable respiratory protection device of claim 2, wherein the at least one fastener is configured to increase blood flow within a face of the user using magnet therapy.

4. The customizable respiratory protection device of claim 1, wherein the filter receiving portion dissipates moisture to an outer surface of the mouth body.

5. The customizable respiratory protection device of claim 1, further comprising:
   a plurality of head fasteners disposed on at least a portion of each edge of the mouth body to wrap around a head of the user.

* * * * *